United States Defensive Publication [19] (H) [11] T104,601

Gilbert [43] Sep. 4, 1984

[54] ALKANEDIYL BRIDGED BENZIMIDAZOLO MONOMETHINE CYANINE DYES, PROCESSES FOR THEIR PREPARATION, AND PHOTOGRAPHIC EMULSIONS AND ELEMENTS CONTAINING SUCH DYES

[76] Inventor: David P. Gilbert, Kodak Park, Rochester, N.Y. 14612

[21] Appl. No.: 570,147

[22] Filed: Jan. 12, 1984

Related U.S. Application Data

[62] Division of Ser. No. 471,615, Mar. 3, 1983.

[51] Int. Cl.[3] ..... C07D 235/04

[52] U.S. Cl. ..... 548/328; 260/245.6; 544/245

[57] ABSTRACT

Alkanediyl bridged benzimidazolo monomethine cyanine dyes are disclosed wherein at least one benzimidazolo nucleus is provided with an electron-withdrawing group. A disclosed preparation of the dyes includes producing an electron-withdrawing group substituted bis(2-nitrophenyl)-2-$R^1$-propanediamide, where $R^1$ is hydrogen or alkyl; converting the nitro groups to primary amine substituents; removing the elements of water to effect ring closure; and thereafter providing the —$CR^1$— linked benzimidazole nuclei so formed with an N,$N^1$-alkanediyl bridging group and quaternizing substituents. Dye synthesis is completed by reducing the —$CR^1$— linking group to the corresponding methine. The dyes are useful as sensitizers in silver halide emulsions and photographic elements.

3 Claims, No Sheets Drawing,

33 Pages Specification

The file of this unexamined application may be inspected and copies thereof may be purchased (849 O.G. 1221, Apr. 9, 1968).